United States Patent [19]

Beauquey et al.

[11] Patent Number: 5,571,458
[45] Date of Patent: Nov. 5, 1996

[54] WASHING COMPOSITION FOR KERATIN FIBRES WHICH IS BASED ON CHITOSAN-DERIVED POLYMERS

[75] Inventors: Bernard Beauquey, Clichy; Sandrine Decoster, Epinay-sur-Seine, both of France

[73] Assignee: L'Oreal, Paris, France

[21] Appl. No.: 281,544

[22] Filed: Jul. 28, 1994

[30]  Foreign Application Priority Data

Jul. 28, 1993 [FR] France ................................ 93 09299

[51] Int. Cl.$^6$ ................ C11D 1/94; C11D 3/37; A61K 7/075
[52] U.S. Cl. .................. 510/125; 424/70.1; 424/70.11
[58] Field of Search ................ 252/174.23, 549, 252/544, 552, 556, 547, 554, DIG. 2, DIG. 5, DIG. 7, DIG. 13; 536/20; 514/881, 846, 55; 424/70.1, 70.11

[56]  References Cited

U.S. PATENT DOCUMENTS

| | | | |
|---|---|---|---|
| 4,402,977 | 9/1983 | Grollier et al. | 424/70 |
| 4,923,977 | 8/1990 | Lang et al. | 536/20 |
| 4,976,952 | 12/1990 | Lang et al. | 424/47 |
| 4,996,059 | 2/1991 | Grollier et al. | 424/71 |
| 5,100,656 | 3/1992 | Lang et al. | 424/70 |
| 5,275,755 | 1/1994 | Sebag et al. | 252/174.15 |

FOREIGN PATENT DOCUMENTS

| | | |
|---|---|---|
| 0277322 | 8/1988 | European Pat. Off. . |
| 0437114 | 7/1991 | European Pat. Off. . |
| 0526279 | 2/1994 | European Pat. Off. . |
| 62-138418 | 6/1987 | Japan . |
| 03005414 | 1/1988 | Japan . |
| 63-277608 | 11/1988 | Japan . |
| 8805812 | 8/1988 | WIPO . |
| 9201777 | 2/1992 | WIPO . |

*Primary Examiner*—Paul Lieberman
*Assistant Examiner*—Lorna M. Douyon
*Attorney, Agent, or Firm*—Jacobson, Price, Holman & Stern, PLLC

[57]  ABSTRACT

A washing composition suitable for washing keratin fibres contains at least one anionic surfactant containing one or more sulphonate groups, at least one surfactant from the family of the betaines and at least one chitosan-derived polymer, the ratio of anionic surfactant to betaine-type surfactant being greater than 0.7.

8 Claims, No Drawings

WASHING COMPOSITION FOR KERATIN FIBRES WHICH IS BASED ON CHITOSAN-DERIVED POLYMERS

BACKGROUND OF THE INVENTION

1. Field of the Invention

The present invention relates to a composition intended for washing and for the treatment of keratin fibres, more particularly of hair, and to washing processes using such a composition.

2. Discussion of Related Art

Chitosan-derived polymers are well known in the art and have already been recommended for use in compositions for the treatment of keratin fibres, especially hair, with a view to improving their appearance in the course of time. Such compositions are described, more particularly, in French Patents FR-2,486,394 and FR-2,470,596.

Such polymers have also been used in compositions which contain, especially, sodium lauryl ether sulphate or ammonium lauryl sulphate and which are intended to act against greasy appearance of the hair. However, these compositions do not allow the hairstyle to stay properly.

Compositions for washing hair or shampoos are generally formulated on the basis of anionic surfactants which are good detergents and good foaming agents, or using amphoteric surfactants, which are gentler, but more expensive.

Although the anionic or amphoteric surfactants or combinations of these allow the hair to be cleansed, the hairstyle will usually stay poorly. This problem is conventionally solved by applying, after shampooing, a lotion which contains a polymer which is capable of acting on the hair in such a way that the hairstyle stays.

It has also been envisaged to introduce polymers, in particular cationic, amphoteric and anionic polymers or mixtures of these, into shampoos based on anionic surfactants of the sulphate family. However, there are solubilization problems, and when solubilization is obtained, the hairstyle does not always stay satisfactorily.

DESCRIPTION OF THE INVENTION

The applicant has discovered, and this is the subject of the invention, that, by combining an anionic surfactant from the sulphonate family, a surfactant from the family of the betaines and a chitosan-derived amphoteric polymer in an aqueous medium, it was possible to obtain a homogenous washing composition which has, at the same time, good detergent properties and acts on the hair in such a way that the hairstyle stays well once the hair is washed and dried.

Washing compositions which contain such a combination are therefore a subject of the invention.

Another subject of the invention is a process for washing and treating keratin fibres, in particular hair, using the above-described composition.

Other subjects of the invention will come to light upon reading the description and the examples which follow.

The washing composition for keratin fibres, in particular hair, according to the invention is essentially characterized by the fact that it contains, in an aqueous medium suitable for washing:

a) at least one anionic surfactant having one or more sulphonate groups, b) at least one betaine-type surfactant, and c) a chitosan-derived polymer; the ratio between anionic surfactant and betaine-type surfactant being equal to, or greater than, 0.7.

The ratio between anionic and betaine-type surfactant is preferably between 0.7 and 4.

The composition according to the invention does not contain a cationic and/or anionic polymer.

More particularly, the anionic surfactants from the family of the sulphonates are selected amongst the alkali metal salts, alkaline earth metal salts, amine salts, ammonium salts, amino alcohol salts, $\alpha$-olefin sulphonates, alkylsulphosuccinates, alkyl ether sulphosuccinates, alkylamidosulphosuccinates which are optionally oxyethylenated with 1 to 10 mols of ethylene oxide and in which the alkyl group preferably contains 8 to 18 carbon atoms, acylisethionates and N-acyltaurines.

The betaine-type surfactants are more particularly selected from amongst the alkylbetaines and alkylsulphobetaines having 8 to 18 carbon atoms in the alkyl group and the alkylamidopropylbetaines having between 5 and 15 carbon atoms in the alkyl group.

The chitosan-derived polymers contain, in particular, units of the following formulae:

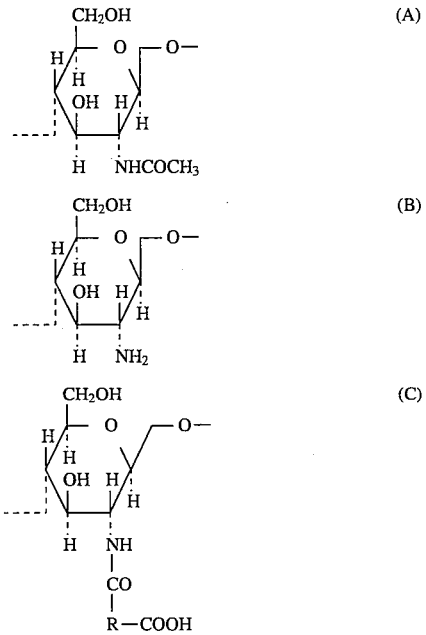

in which unit (A) is present in ratios of between 0 and 30% by weight, unit (B) is present in ratios of between 5 and 50% by weight and unit (C) is present in ratios of between 30 and 90% by weight.

In formula (C), R represents a radical of the formula:

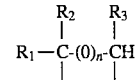

in which n is zero or 1; if n is zero, $R_1$, $R_2$ and $R_3$ are identical or different and each is a hydrogen atom, a methyl, hydroxyl, acetoxy or amino group, an alkylthio radical whose alkyl group contains an amino group or a monoalkylamine or dialkylamine radical, it being possible for the monoalkylamine and dialkylamine radicals to be interrupted by one or more nitrogen atoms and/or substituted by one or more amino, hydroxyl, carboxyl, alkylthio or sulpho groups, in which case at least one of the radicals $R_1$, $R_2$ and $R_3$ is a hydrogen atom; if n is 1, each of the radicals $R_1$, $R_2$ and $R_3$ represents a hydrogen atom.

Alkyl is preferably a group having 1 to 6 carbon atoms.

The polymer composed of units (A), (B) and (C) or (B) and (C) hereinabove can also exist in the form of a salt formed together with a cosmetically acceptable base or acid.

More particularly preferred chitosan-derived polymers are those containing 0 to 20% by weight of unit (A), 40 to 50% by weight of unit (B) and 40 to 50% by weight of unit (C), in which R is a radical $CH_2$—$CH_2$—.

These polymers are known per se and can be prepared, especially, by acylation of chitosan with an acid anhydride, such as described in French Patent FR 2,137,684.

The aqueous medium can be composed solely of water or of a mixture of water and a cosmetically acceptable solvent, such as a $C_1$–$C_4$ lower alcohol, such as ethanol, isopropanol or n-butanol; alkylene glycols, such as ethylene glycol, and glycol ethers. The pH of these compositions is generally between 3 and 9, more particularly between 4 and 8.

The surfactants are used in the compositions according to the invention in amounts which suffice to impart a detergent character to the composition, and they are between 5 and 50% relative to the total weight of the composition, in particular between 8 and 35%, the ratio between the anionic surfactants of the family of the sulphonates and the surfactants of the family of the betaines being greater than 0.7, preferably between 0.7 and 4.

In general, the chitosan-derived polymers are used in the compositions according to the invention in amounts of between 0.1 and 5% by weight, in particular between 0.25 and 2% by weight relative to the total weight of the composition.

Particularly preferred compositions according to the invention contain:

a) 4 to 8% of alkylsulphosuccinate, b) 3 to 7% of α-olefin sulphonate, c) 2.5 to 10% of an alkylbetaine, and d) 0.5 to 5% of chitosan derivatives, as defined above the ratio between alkylsulphosuccinate plus α-olefin sulphonate and alkylbetaine being between 0.7 and 4.

In a preferred embodiment, the ratio of anionic surfactants having a sulphonyl to the betaine-type surfactants is between 1 and 3.

The above-defined washing compositions can also contain, in addition to the above-defined combination, additives which are conventionally used in shampoos, such as viscosity regulators, such as electrolytes, hydrotropes or other thickening agents. More particularly, the following may be mentioned: sodium chloride, sodium xylenesulphonate, scleroglucans, xanthan gums, coconut acid alkanolamides, alkyl ether carboxylic acid alkanolamides which are optionally oxyethylenated with up to 5 mols of ethylene oxide. These viscosity regulators are used in the compositions according to the invention in amounts of up to 10% by weight relative to the total weight of the composition.

The compositions according to the invention can also contain up to 3% of pearlescent or opacifying agents which are well known in the art, such as sodium palmirate or magnesium palmitate, sodium stearate, sodium hydroxystearate, magnesium stearate or magnesium hydroxy-stearate, ethylene glycol monostearate or ethylene glycol distearate, or ethers of fatty alcohols having 27 to 44 carbon atoms.

These compositions can also contain other agents which are intended to improve the cosmetic properties of the hair without, however, changing the stability of the compositions, such as cationic surfactants, non-ionic polymers or proteins. In a preferred embodiment of the invention, the composition does not contain silicone having a hydroxyaryl amino group.

They can also contain various adjuvants conventionally used in cosmetology, such as perfumes, preservatives, sequestering agents, foam stabilizers or acidifying or alcalinizing agents which are well known in cosmetoloy.

The process for washing keratin fibres, in particular human hair, according to the invention is essentially characterized in that at least one composition as defined hereinabove is applied to the wet hair, whereupon, after massage and, if appropriate, leaving the hair for a few minutes, the hair is rinsed. After drying and styling, it is found that the hairstyle stays very well.

The examples which follow are intended to illustrate the invention without, however, imposing any limitation.

EXAMPLE 1

| | |
|---|---|
| Oxyethylenated disodium lauryl ether sulphosuccinate (1 to 4 mols of ethylene oxide), commercially available at 40% A.I. under the name "SETACIN 103 SPECIAL" from ZSCHIMMER & SCHWARZ | 6 g of A.I. |
| α-olefin sulphonate, commercially available at 38% A.I. under the name "ELFAN OS 46" from AKZO | 4.6 g of A.I. |
| Coconut amidopropylbetaine, commercially available at 30% A.I. under the name "TEGO BETAIN HS" from GOLDSCHMIDT | 3.6 g of A.I. |
| Polymer A | 1 g |
| HCl qs pH = 5.3 | |
| Water qs | 100 g |

As shown by the curl crushing test described hereinbelow, the style of the treated hair stays better.

Polymer A has the formula below and contains units B and C in a ratio of 50/50 by weight.

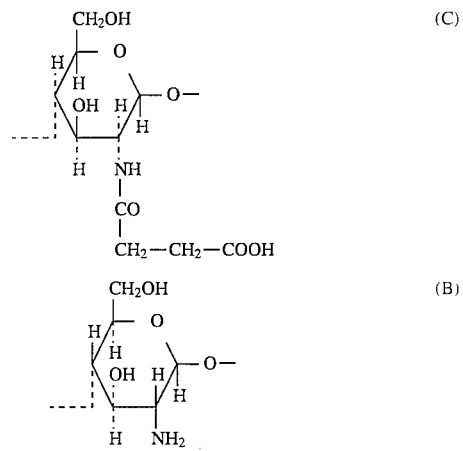

EXAMPLE 2

| | |
|---|---|
| Oxyethylenated disodium lauryl ether sulphosuccinate (1 to 4 mols of ethylene oxide), commercially available at 40% A.I. under the name "SETACIN 103 SPECIAL" from ZSCHIMMER & SCHWARZ | 6 g of A.I. |
| α-olefin sulphonate, commercially available at 38% A.I. under the name "ELFAN OS 46" from AKZO | 4.6 g of A.I. |

-continued

| | |
|---|---|
| Coconut amidopropylbetaine, commercially available at 30% A.I. under the name "TEGO BETAIN HS" from GOLDSCHMIDT | 3.6 g of A.I. |
| Polymer A | 2 g |
| HCl qs pH = 5.3 | |
| Water qs | 100 g |

As shown by the curl crushing test described hereinbelow, the style of the treated hair stays better.

Polymer A has the formula above and contains units B and C in a ratio of 50/50 by weight.

EXAMPLE 3

| | |
|---|---|
| Oxyethylenated disodium lauryl ether sulphosuccinate (1 to 4 mols of ethylene oxide), commercially available at 40% A.I. under the name "SETACIN 103 SPECIAL" from ZSCHIMMER & SCHWARZ | 6 g of A.I. |
| α-olefin sulphonate, commercially available at 38% A.I. under the name "ELFAN OS 46" from AKZO | 4.6 g of A.I. |
| Coconut amidopropylbetaine, commercially available at 30% A.I. under the name "TEGO BETAIN HS" from GOLDSCHMIDT | 10.6 g of A.I. |
| Polymer A | 2 g |
| HCl qs pH = 5.3 | |
| Water qs | 100 g |

As shown by the curl crushing test described hereinbelow, the style of the treated hair stays better.

Polymer A has the formula above and contains units B and C in a ratio of 50/50 by weight.

CURL CRUSHING TEST

The test compositions are applied flat to 6 tufts of hair of 2.5 g each at a rate of 0.6 g per tuft. The rinsed and wrung-out tufts are rolled in contiguous turns onto a solid roller of diameter 20 mm, where they are held in place by an elastic on each end of the roller.

The tufts are dried under a drying hood for 45 minutes at 60° C. They are then allowed to stabilize for 1 hour at ambient temperature. Then, they are removed gently from the roller without altering their shape.

The curl is placed longitudinally into a cradle connected to a resistance strain gauge. Onto the curl there is lowered a horizontal iron rod which presses it down and reduces it to a constant thickness of approximately 15 mm. The gauge displays the crushing force in grammes. Each curl is measured four times, while its position is changed each time. Measurements are carried out on 6 tufts per composition.

The mean values obtained are shown in Table 1 hereinbelow.

| | Example 1 | Example 2 | Example 3 |
|---|---|---|---|
| Mean of 4 measurements on 6 tufts | 431 | 460 | 498 |

When the same measurements are taken using the compositions described in Examples 1 or 2, but without polymer A, a value of 256 is obtained.

We claim:

1. A washing composition which is free from cationic and anionic polymers, comprising, in an aqueous medium suitable for washing keratin fibres, at least one anionic surfactant having one or more sulphonate groups, at least one surfactant from the family of the betaines and at least one chitosan-derived polymer, the weight ratio of anionic surfactant to betaine surfactant being between 0.7 and 4, the at least one anionic surfactant, the at least one betaine surfactant, and the at least one chitosan-derived polymer each being present in the composition in an amount effective for washing and styling keratin fibres, said chitosan-derived polymer contains monomer units of the following formula:

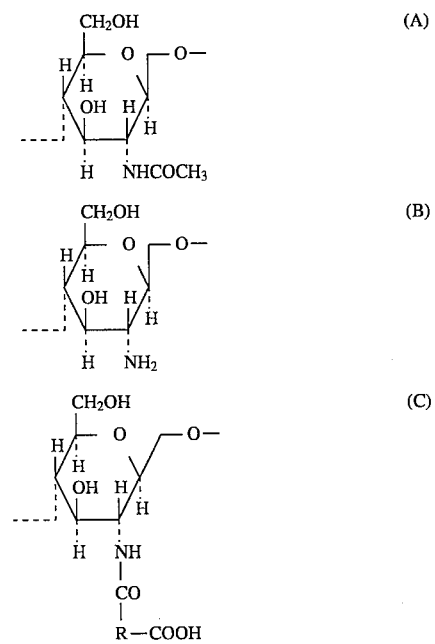

in which unit (A) is present in ratios of between 0 and 30% by weight, unit (B) is present in ratios of between 5 and 50% by weight and unit (C) is present in ratios of between 30 and 90% by weight; in formula (C) R is represents a radical of the formula:

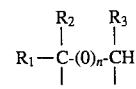

in which n is zero or 1; if n is zero, $R_1$, $R_2$ and $R_3$ are identical or different and each is a hydrogen atom, a methyl, hydroxyl, acetoxy or amino group, an alkylthio radical whose alkyl group contains an amino group or a monoalkylamine or dialkylamine radical, it being possible for the monoalkylamine and dialkylamine radicals to be interrupted by one or more nitrogen atoms or substituted by one or more amino, hydroxyl, carboxyl, alkylthio or sulpho groups, in which case at least one of the radicals $R_1$, $R_2$ and $R_3$ represents a hydrogen atom; if n is 1, each of the radicals $R_1$, $R_2$ and $R_3$ represents a hydrogen atom, it being possible for these polymers to be present in the form of a salt formed together with a cosmetically acceptable base or acid.

2. Composition according to claim 1, wherein the anionic surfactants which contain sulphonate groups are alkali metal salts, alkaline earth metal salts, amine salts, ammonium salts, amino alcohol salts, α-olefin sulphonates, alkylsulphosuccinates, alkyl ether sulphosuccinates, alkylamidosulphosuccinates which are optionally oxyethylenated with 1 to 10 moles of ethylene oxide acylisethionates or N-acyltaurines.

3. Composition according to claim 1, wherein the betaine surfactants are alkylbetaines or alkylsulphobetaines having a carbon number of between 8 and 18, or alkylamidopropylbetaines having a carbon number of between 5 and 15.

4. Composition according to claim 1, wherein the chitosan-derived polymer contains 0 to 20% by weight of unit (A), 40 to 50% by weight of unit (B) and 40 to 50% by weight of unit (C) in which R is the radical —$CH_2$—$CH_2$—.

5. Composition according to claim 1, wherein the at least one anionic surfactant and the at least one betaine surfactant are each present in the composition in an amount of between 5 and 50% by weight relative to the total weight of the composition.

6. Composition according to claim 1, wherein the at least one chitosan-derived polymer is present in the composition in an amount of between 0.1 to 5% by weight relative to the total weight of the composition.

7. Composition according to claim 1, wherein it contains:

4 to 8% of alkylsulphosuccinate, 3 to 7% of α-olefin sulphonate, 2.5 to 10% of an alkylbetaine, and 0.5 to 5% of chitosan derivatives.

8. Process of washing keratin fibres, wherein the composition as defined in claim 1 is applied to wet fibres, and the hair is then rinsed.

* * * * *